United States Patent [19]

Blake

[11] Patent Number: 5,869,047
[45] Date of Patent: Feb. 9, 1999

[54] METHODS FOR THERAPEUTICALLY TREATING IMMUNOCOMPRISED PERSONS

[75] Inventor: Milan Blake, Silver Spring, Md.

[73] Assignee: Blake Laboratories, Inc., Great Neck, N.Y.

[21] Appl. No.: 734,941

[22] Filed: Oct. 22, 1996

[51] Int. Cl.$^6$ ................................................ A61K 39/09
[52] U.S. Cl. ...................................... 424/140.1; 530/413
[58] Field of Search ............................ 424/140.1, 178.1, 424/179.1; 530/350, 380, 412, 413; 604/4, 5, 6

[56] References Cited

U.S. PATENT DOCUMENTS

| | | | |
|---|---|---|---|
| 4,223,672 | 9/1980 | Terman et al. | 128/214 R |
| 4,757,134 | 7/1988 | Blake et al. | 530/350 |
| 4,801,449 | 1/1989 | Balint, Jr. et al. | 424/85.8 |
| 5,122,112 | 6/1992 | Jones | 604/4 |
| 5,210,183 | 5/1993 | Lindahl et al. | 530/350 |
| 5,413,918 | 5/1995 | Faulmann | 435/69.1 |

OTHER PUBLICATIONS

Apicella, M.A. et al. (1986) "Bactericidal Antibody Response of Normal Human Serum to the Lipooligosaccharide of *Neisseria gonorrhoeae*," *The Journal of Infectious Diseases*, Vol. 153, No. 3, Mar. pp. 520–526.
Birx, D.L. et al. (1991) "Immunologic Parameters in Early–Stage HIV–Seropositive Subjects Associated with Vaccine Responsiveness," *Journal of Acquired Immune Deficiency Syndromes*, 4:188–196.
Conlon, C.P. (1993) "The immunocompromised traveller," *British Medical Bulletin*, Vol. 49, No. 2, pp. 412–422.
Eckrich, R.J. et al. (1993) "Laboratory tests to exclude IgA deficiency in the investigation of suspected anti–IgA transfusion reactions," *Transfusion*, Vol. 33,No. 6, pp. 488–492.
Filipovich, A..H., et al. "Lymphoproliferative Disorders and Other Tumors Complicating Immunodeficiencies," *Immunodeficiency*, Vol. 5, pp. 91–112.
Griffis, J.M. (1975) "Bactericidal Activity of *Meningococcal Antisera,*" *The Journal of Immunology*, Vol. 114, No. 6, Jun., pp. 1779–1784.
Griffis, J.M. and M.A. Bertram (1977) "Immunoepidemiology of Meningococcal Disease in Military Recruits. II. Blocking of Serum Bactericidal Activity by Circulating IgA Early in the Course of Invasive Disease," *The Journal of Infectious Diseases*, Vol. 136, No. 6, Dec., pp. 733–739.
Griffis, J.M. (1982) "Serum IgA: Modulation of Complement Activation and Induction of Susceptibilty to Bacterial Dissemination," *Infection* 10, Nr. 4, pp. 246–251.
Griffis, J.M. (1983) "Biologic Function of the Serum IgA System: Modulation of Complement–Mediated Effector Mechanisms and Conservation of Antigenic Mass, " *Annals New York Academy of Sciences*, pp. 697–707.
Griffis, J.M. (1983) "IgA Blocks IgM and IgG–Initiated Immune Lysis by Separate Molecular Mechanisms," *The Journal of Immunology*, Vol. 130, No. 6, Jun., pp. 2882–2885.
Jerlström, P.G. et al. (1991) "The IgA–binding β antigen of the c protein complex of Group B streptococci: sequence determination of its gene and detection of two binding regions," *Molecular Microbiology*, 5(4), 843–849.
Lim, E.C. et al. (1993) "In Vitro Studies to Explain High Renal Allograft Survival in IgA Nephropathy Patients," *Transplantation*, Vol. 55, No. 5, May, 996–999.
Misbah, S.A. and H.M. Chapel (1993) "Adverse Effects of Intravenous Immunoglobulin," *Drug Safety* 9 (4): 254–262.
Musher, D.M. et al. (1984) "Immunoglobulin A from Bronchopulmonary Secretions Blocks Bactericidal and Opsonizing Effects of Antibody to Nontypable *Haemophilus influenzae*, "*Infection and Immunity*, Vol. 45, No. 1, Jul., pp. 36–40.
Quesnal, A. et al. (1994) "Is there IgA of gut mucosal origin in the serum of HIV1 infected patients?" *Gut*, 35: 803–808.
Quesnal, A. et al. (1994) "Early impairment of gut mucosal immunity in HIV–1 infected children,"*Clin Exp Immunol*, 97:380–385.
Rhoads, J.L. et al. (1991) "Safety and Immunogenicity of Multiple Conventional Immunizations Administered During Early HIV Infection," *Journal of Acquired Immune Deficiency Syndromes*, 4:724–731.
Russell–Jones, G.J. et al. (1980) "The Ability to IgA to Inhibit the Complement–Mediated Lysis of Target Red Blood Cells Sensitized With IgG Antibody, "*Molecular Immunology*, Vol. 17 pp. 1173–1180.
Russell–Jones, G.J. et al. (1981) "Inhibition of Cutaneous Anaphylaxis and Arthus Reactions in the Mouse by Antigen Specific IgA,"*Int. Archs Alergy appl. Immun.* 66:316–325.
Sandler, S.G. et al. (1995) "IgA Anaphylactic Transfusion Reactions," *Transfusion Medicine Reviews*, Vol IX, No 1, Jan. pp. 1–8.
Taylor, P.W. (1972) "An Antibacteriocidal Factor in the Serum of Two Patients with Infections of the Upper Urinary Tract,"*Clinical Science* 43, 23–30.

*Primary Examiner*—Robert D. Budens
*Attorney, Agent, or Firm*—Saliwanchik, Lloyd & Saliwanchik

[57] ABSTRACT

The subject invention pertains to methods of treating immunocompromised patients, such as individuals infected with HIV, that exhibit elevated levels of IgA relative to IgG. The use of IgA-binding compositions immobilized onto a support matrix to extracorporeally remove IgA molecules from a sample or biological fluid for therapeutic purposes is provided by the present invention. The subject invention further pertains to novel polypeptides which bind in a specific manner to human IgA. The polypeptides of the present invention comprise an IgA-binding region from an IgA-binding protein of Group B streptococcal bacteria.

12 Claims, 2 Drawing Sheets

METHODS FOR THERAPEUTICALLY TREATING IMMUNOCOMPRISED PERSONS

FIELD OF THE INVENTION

The present invention concerns human immunity, circulating antibodies, and extracorporeal devices. The invention relates, in particular, to methods and means for treating HIV-infected and other immunocompromised individuals by selectively removing immunoglobulin A (IgA) from the systemic circulation of patients.

BACKGROUND OF THE INVENTION

The immune system of mammals, and specifically humans, is a finely balanced interaction between cellular responses and molecular responses. Cellular responses include reactions initiated by phagocytes, monocytes, and cytotoxic T cells. Molecular responses include the production of immunoglobulins, antibodies, initiation of complement, etc. It is the responsibility of the immune system in this coordinated effort to form a barrier between self and non-self and to protect us against invasion of external potentially harmful substances. Nonetheless, animals routinely consume a multitude of foreign material in the form of nutrients and inhale numerous foreign airborne particles. Reproduction of mammalian life itself depends on a female being impregnated with an egg fertilized by sperm, in essence a foreign body to the female, and carrying a child internally for nine months only partially like herself. In the vast majority of individuals, these daily exposures to foreign matter elicit little, if any, noticeable immune activity. Much of our understanding of the function of each part of the immune system has come from the study of individuals who lack some particular component or who are deficient in a specific activity. While some imbalances within this complex coordinated endeavor can be compensated for and tolerated by the host, others lead to unhealthy, dangerous conditions.

The subdivision of the immune system which seems to be the most well poised to maintain this equilibrium is located just below the mucosal epithelium throughout the body and is collectively known as the mucosal immune network. The mucosal immune network accounts for over 85 percent of all lymphoid tissue and specializes not only in acting as a deterrent to keep foreign matter from entering the body but also prevents over-stimulation of the systemic immune system. Excessive stimulation of the systemic immune system often results in bystander tissue damage and destruction.

The major immunoglobulin produced by the mucosal immune network is immunoglobulin A (IgA) which is secreted by activated, differentiated lymphocytes in the lamina propria. The structure and function of IgA is quite distinct from that of systemically produced immunoglobulin G (IgG). These differences in structure and function of IgA are in accordance with the major objectives of mucosal immunity. Firstly, IgA molecules occur predominantly as dimers and tetramers and have four to eight antigen-binding sites. This increase in binding-site density is one explanation for the greater avidity of IgA for foreign antigens as compared to that of IgG. Secondly, increased glycosylation of IgA molecules helps to protect them from proteolytic digestive enzymes found in the gut. Thirdly, IgA molecules also contain regions important for their active displacement from the lamina propria to the outside of the body. This active transport mechanism seems to perform two important functions. It maintains the largest amount of IgA at the site of highest exposure to foreign substances, for example, on the surfaces of the gastrointestinal, pulmonary, and urogenital tracts. It has been shown that IgA present on these surfaces inhibit binding and subsequent penetration of pathogens and allergens across the epithelial cell boundary. If by chance some foreign material does breach the epithelium, the second important function of the active transport mechanism is to bind the antigen either within epithelial cells or in the lamina propria and to remove it from the body via excremental pathways.

Another important function of IgA is to keep the responsiveness of the immune system to a minimum. However, the ability of the immune system to intensify at times is clearly important. This happens, for example, when physical injury occurs or when an accumulation of pathogens overwhelms the mucosal immunity. Yet obviously this intense activity cannot and should not occur every time an animal consumes food. Nor should such intensity, once initiated, remain sustained over long periods of time. However, once the immune system is activated, IgA down-regulates this activity as soon as possible in order to regain the proper and healthy equilibrium in the immune system. IgA molecules accomplish this task by intervention into the complement cascade.

In conjunction with systemic immunity and IgG, the complement system is a group of proteins which, through a progression of reactions, amplify and intensify immunological responses. It has been shown that IgG molecules aligned in close proximity initiate the reaction. This can occur, for example, when IgG molecules attach to bacteria or other foreign bodies. The end product of this reaction, called the membrane act complex or MAC, inserts itself into the invading organism causing cell lysis and death.

When levels of IgA are diminished or completely lacking, the complement cascade can be initiated. In carefully controlled studies, it has been demonstrated that by the addition and subsequent interdigitation of a relatively few IgA molecules between molecules of IgG, the complement cascade can be inactivated (Russell-Jones et al. 1980). This in turn down-regulates all subsequent immune activation events. In addition, the ability of IgA to minimize cellular immune responses is less well documented but nonetheless evident (Russell-Jones et al. 1981).

Examples of what results when the mucosal immune system becomes imbalanced have been reported. The simplest, most easily identified irregularity of the mucosal immune system is the complete absence, or reduced production, of IgA. The frequency of this condition has been reported as high as 1 out of every 400 individuals (Eckrich et al. 1993; Sandler et al. 1995). Patients exhibiting diminished or non-existent levels of IgA reveal themselves by having an inordinate number of allergies and allergic reactions. Such individuals are also frequently identified with severe serum reactions following blood transfusions and gamma globulin therapy (Sandler et al. 1995; Misbah & Chapel, 1993; Dabrow & Wilkins, 1993).

At the other end of the spectrum, the elevation of IgA has been, until recently, less frequently observed. Indeed, scientists interested in exploiting the mucosal immune system for vaccine purposes have been frustrated by the inability to mount and sustain a significant, specific IgA response. Most often, IgA has been studied in isolation and out of context with the other components of the immune system. These studies have shown that IgA can bind to and inhibit the interactions of pathogens within human cells and tissue. Ways to increase IgA activity against pathogens has been a major avenue of research.

Although the ratio of IgA to IgG for a specific antigen usually remains within a relatively narrow range, variations in this ratio have been reported. A recent study demonstrated that patients with increased levels of IgA reactive to their foreign, transplanted kidneys had significantly lower rates of rejection compared with patients with lower IgA levels (Lim et al. 1993). The investigators proposed that anti-HLA IgA antibody contributed to the high kidney graft survival in patients with elevated IgA by blocking IgG antibodies or inhibiting cellular immune responses. This study suggested that elevated levels of IgA may have an impact on cellular responses of the immune system and graft rejection.

The effects of abnormally elevated IgA/IgG ratios have also been described by researchers studying an outbreak of bacterial meningitis in Seattle, Wash. (Griffiss & Bertram, 1977; Griffiss, 1975; Griffiss, 1983; Griffiss & Goroff, 1983; Griffiss, 1982). These studies showed that the majority of patients in this outbreak had elevated levels of IgA reactive to the invading meningococcal pathogens compared to uninfected controls and that sera from these patients were unable to kill the bacteria. However, after the IgA was removed from the patients' sera, the serum was then able to destroy the bacteria. It was felt that these patients were originally normally immune and had the ability to destroy as well as resist infection by these pathogens, but, due to an immune response of unknown origin, the IgA/IgG ratio became imbalanced and the increased anti-meningococcal IgA may have interfered with the ability of systemic IgG and complement to eliminate these organisms. Similar effects have been observed for other pathogenic bacteria (Apicella et al. 1986; Musher et al. 1984; Taylor, 1972). Elevation in specific IgA antibodies reactive to tumor antigens has been observed in women with malignant ovarian carcinomas as compared with normal women or women with benign tumors (Gupta et al. 1994). In addition, a statistically significant correlation has been found with increased levels of IgA antibody reactive to the Epstein-Barr virus and the appearance of esophageal cancer in patients from Southeast Asia (Filipovich et al. 1994).

All of the reports referred to above have focused on elevations in the levels of IgA immunoreactive to a specific antigen. Thus, in most cases, the concentration of IgA antibody to a specific antigen was increased, but the overall total concentration of IgA was not increased. An association between elevated levels of IgA has been observed in nephropathy and kidney disease (Lim et al. 1993), but the genesis of this IgA is unknown. Recently, it has been demonstrated that HIV seropositive individuals have a statistically significant increase in IgA as they progress into AIDS, whereas serum levels of other immunoglobulins remain normal (Quesnel et al. 1994a; Quesnel et al. 1994b; Anonymous, 1994). The concentration of IgA continued to rise in these patients and upon their death was several hundred-fold above normal levels. How this elevation in IgA affects all of the symptoms and diseases which afflict AIDS patients is unknown. It has been shown in isolated instances that vaccination to increase systemic IgG levels improves the specific immunity for which the vaccine was made (Conlon, 1993; Birx et al. 1991; Rhoads et al. 1991; Guerra et al. 1992). However, it is impossible to raise systemic IgG antibody levels to each of the antigens to which the IgA levels have become elevated.

The ability to accomplish extracorporeal removal of certain components from bodily fluids without increased risks to the patient has been established. Although extracorporeal devices, such as kidney dialysis machines, are known in the art and have been shown to be therapeutically effective in eliminating abnormally high concentrations of certain components of serum, none of these extracorporeal devices are directed to specifically removing IgA from blood or serum. Moreover, there is no teaching or suggestion in the art directed to the extracorporeal removal or reduction of IgA from biological fluids as a therapeutic treatment for immunocompromised patients, particularly those patients that are infected with HIV. U.S. Pat. No. 4,801,449 which issued to Balint, Jr. et al. discloses an immunoadsorbent material comprising Protein A for removing IgG from biological fluids as a method for treating Kaposi's sarcoma. U.S. Pat. No. 5,122,112, which issued to Jones teaches a method for treating antigen-related disease by identifying the predominant antigen associated with the disease and then using an antigen-specific immunoadsorbent to remove the antigen from a patient's system.

BRIEF SUMMARY OF THE INVENTION

The subject invention concerns methods for therapeutically treating immunocompromised patients, such as persons infected with HIV. Specifically, the subject invention pertains to methods for removing and depleting IgA molecules from a bodily fluid in a therapeutically effective manner of a patient in need of such treatment. The subject methods comprise the use of compositions that are capable of binding IgA, such as Protein B, or biologically active fragments thereof, as an IgA-specific immunoadsorbent as described herein. Fluids containing IgA, such as serum, are obtained from the patient and then contacted with the IgA-binding immunoadsorbent. IgA antibodies present in the fluid are bound by the immunoadsorbent and removed from the fluid. The IgA depleted fluid can then be returned to the patient.

The subject invention also concerns the discovery of novel materials and methods useful for binding to and removing IgA molecules in a sample or biological fluid. Specifically, the subject invention concerns polypeptides corresponding to a portion of the Protein B molecule that binds to the Fc region of IgA molecules. The subject invention further concerns immunoadsorbents which have IgA-binding compositions immobilized on a support matrix.

BRIEF DESCRIPTION OF THE SEQUENCES

Figure 1A:
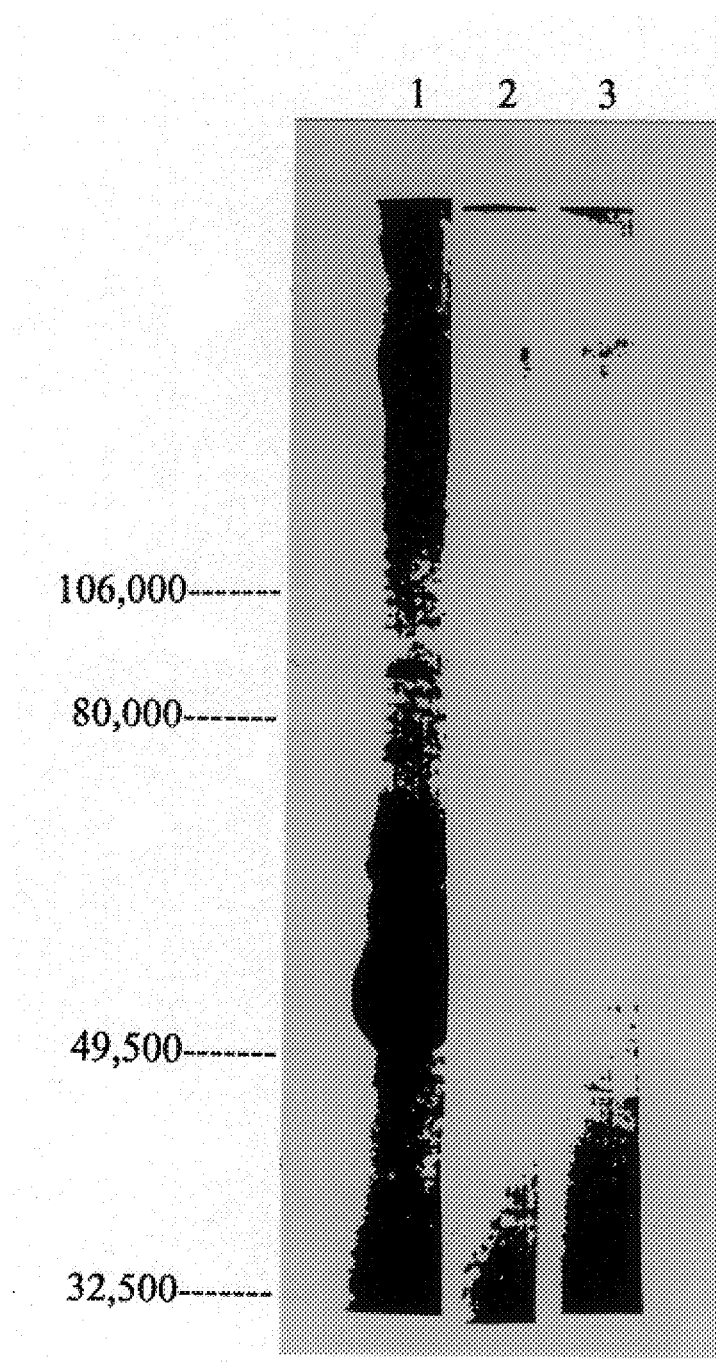
FIGS. 1A and 1B show an SDS-PAGE and Western Blot analysis, respectively, of IgA purified by protein B affinity chromatography. Coomassie stain (Panel A) and anti-alpha chain specific immunoreactivity (Panel B) of electroblotted SDS-PAGE separated human serum (lane 1), affinity column eluted material (lane 2), and commercially available purified IgA are shown.

SEQ ID NO. 1 is an oligonucleotide primer used according to the subject invention.

SEQ ID NO. 2 is an oligonucleotide primer used according to the subject invention.

SEQ ID NO. 3 is an oligonucleotide primer used according to the subject invention.

SEQ ID NO. 4 is an oligonucleotide primer used according to the subject invention.

SEQ ID NO. 5 is an oligonucleotide primer used according to the subject invention.

SEQ ID NO. 6 is a nucleotide sequence that encodes the amino acid sequence of SEQ ID NO. 7.

SEQ ID NO. 7 is the amino acid sequence of an IgA-binding polypeptide of the subject invention.

DETAILED DESCRIPTION OF THE INVENTION

The subject invention concerns methods and materials for treating immunocompromised persons, such as those infected with HIV, by removing or depleting endogenous IgA molecules in a sample or biological fluid using compositions that bind to IgA molecules. The subject invention can be used to restore the proper ratio of IgA to IgG in a patient in need of such treatment. In a preferred embodiment, the method of the subject invention is used to extracorporeally remove, and thereby reduce, excessive levels of IgA in a biological fluid such as plasma or serum, from an HIV-infected patient having elevated IgA levels and in need of such treatment.

In the present invention, an IgA-binding composition coupled to a support matrix can be used to remove or deplete IgA molecules from the biological fluids of a patient in need of effective IgA depletion therapy. Typically, the biological fluid is obtained from the patient and the cellular components, or any other solids, in the biological sample are first separated from the fluid components. For example, blood can be removed from the patient and treated to yield the plasma fraction. The plasma or other biological fluid is then passed over a sterile solid-phase immunoadsorbent support matrix comprising an IgA-binding composition under conditions whereby the coagulation or precipitation of proteins or other molecules in solution is inhibited or prevented by means known in the art. Preferably, the immunoadsorbent specifically binds to IgA antibodies and does not bind other antibody isotypes. IgA present in the fluid binds to the immunoadsorbent, thereby removing the IgA from the fluid. After contacting the fluid with the immunoadsorbent for an effective period of time, the treated fluid can be reinfused back into the patient. The isolated cellular components can also be reinfused into the patient.

The treatment method can be performed in a "batch mode," wherein discrete volumes of fluid are removed from the patient's body, treated according to the subject invention to remove IgA antibody, and reinfused back into the patient after treatment. Alternatively, the method can be performed in a "continuous mode," in which patient fluids are removed from the body, treated according to the subject invention to remove some quantity of IgA, and then the IgA-depleted fluid is reinfused back into the patient's body at the same time that additional fluids are being removed from the patient and treated to remove IgA Optimal quantities of fluid to be treated, as well as frequency or duration of treatment, can be readily determined by the skilled artisan. Thus, a patient may be treated a single time or given multiple treatments over a course of days, weeks, months or years. Extracorporeal treatments to remove IgA can be repeated as necessary to optimize a therapeutic reduction in IgA. The level of IgA reduction to be achieved may necessarily vary for each individual patient. It may not be desirable to remove all or substantially all of the IgA from a patient's system. Typically, a patient is treated according to the subject invention in order to lower elevated IgA concentrations back to normal levels rather than to completely remove all IgA. Although it may be expected that IgA depletion necessary to restore normal IgA to IgG ratios may be therapeutically effective, increased or complete removal of IgA may be required under certain conditions.

Any composition or material that is capable of binding to IgA immunoglobulin is contemplated for use with the subject method. Generally, those compositions that have the highest binding affinity and specificity for IgA are preferred. Suitable known proteins which bind human IgA can be isolated from Streptococcus bacteria. IgA-binding compositions contemplated for use with the subject invention include Protein B, Arp proteins (disclosed in published European Application No. A1 0290707 and A1 0367890), and monoclonal and polyclonal antibodies that bind to IgA. U.S. Pat. No. 5,352,588 discloses an IgA-binding protein from Group A Streptococcus bacteria.

In a preferred embodiment, the IgA-binding composition comprises Protein B, or an IgA-binding fragment thereof. Protein B is an IgA receptor found on certain Group B Streptococci and was first described by Russell-Jones et al. in 1984. The isolation and purification of Protein B has been described in U.S. Pat. No. 4,757,134. A recombinant form of Protein B has been disclosed in U.S. Pat. No. 5,413,918, incorporated herein by reference. In comparisons between Protein B and other reagents which bind human IgA, it has been demonstrated that Protein B possesses several advantageous characteristics. For example, Protein B binds both subclasses of human IgA (Faulmann et al. 1991) and has a much higher affinity for human IgA than many other IgA-binding compositions. In addition, other serum components do not interfere with the binding of Protein B to human IgA, and Protein B is extremely stable under various environmental conditions.

The subject invention further concerns immunoadsorbents comprising IgA-binding compositions immobilized on a solid-phase support matrix and methods for preparing such immunoadsorbents. The IgA-binding composition can be immobilized onto the surface of the support matrix by any method that affixes the IgA-binding composition to the support in a substantially irreversible manner, such as where the composition is covalently bound to the support matrix. In a preferred embodiment, an immunoadsorbent of the subject invention comprises Protein B, or an IgA-binding fragment thereof, coupled to a solid support matrix. More preferably, Protein B can be immobilized on HIPAC (ChromatoChem, Inc., Missoula, MT) or a cross-linked matrix material, such as CNBr-SEPHAROSE (Pharmacia Biotech, Uppsala, Sweden) support matrix. Alternatively, Protein B can be treated with citraconic anhydride to block terminal amines on the protein, after which the Protein B can be immobilized on a matrix, such as an epoxy-activated support. IgA immunoadsorbents of the subject invention can be prepared from a single IgA-binding composition or from a combination of compositions. For example, an IgA-binding immunoadsorbent can be prepared using both Protein B and anti-IgA antibodies coupled to a support matrix.

IgA-binding compositions of the present invention can also be attached or coupled to numerous other support matrices known in the art using standard methods. Suitable solid-phase support matrices can be composed of glass, nylon, particulate silica, polystyrene, polyethylene, polyamides, polyacrylamides, polyvinyls, polypropylene, cellulose agarose, dextran or any other suitable material known in the art. The solid support matrix can be in the form of beads, particles, membranes, or other forms known in the art. Suitable membranes include those composed of nylon, nitrocellulose or polyvinylidene difluoride (PVDF). IgA-binding polypeptides can also be chemically synthesized directly on a solid support matrix using standard peptide synthesis techniques.

IgA-binding immunoadsorbents to be used with the method of the present invention can be employed in known devices that are used for the extracorporeal treatment of biological fluids. For example, U.S. Pat. No. 4,223,672 discloses an apparatus for the withdrawal and extracorporeal treatment of blood from a patient. Extracorporeal devices used with present invention can be prepared, sterilized, and maintained according to standard procedures known in the art.

The subject invention further concerns novel polypeptides that bind specifically to the Fc region of IgA molecules. The polypeptides of the subject invention correspond to a portion of the amino acid sequence of Protein B. The subject polypeptides bind specifically with IgA in a manner comparable to full-length Protein B. One embodiment of the IgA-binding polypeptides of the subject invention comprises the amino acid sequence shown in SEQ ID NO. 7.

The novel IgA-binding polypeptides of the present invention can also be used as a reagent for the binding, separation, and/or identification of IgA in a sample. The polypeptides can also be used in a variety of assays known in the art. For example, the polypeptides can be used in ELISAs, RIA, and other immunoassays according to standard techniques. The subject polypeptides can also be used to detect and identify IgA on dot-blots and Western blots. The polypeptides of the subject invention can also be coupled to a solid-phase support and used to prepare purified IgA compositions from crude mixtures via standard affinity chromatography methods.

A further aspect of the subject invention concerns immunospecific antibodies generated using the novel IgA-binding polypeptides of the present invention, such as those polypeptides having the same or substantially the same amino acid sequence as shown in SEQ ID NO. 7. Antibodies that are immunoreactive with the IgA-binding polypeptides can be produced by immunizing a host animal using standard procedures well known in the art. The antibodies thus produced can be isolated and purified. The antibodies can be either monoclonal or polyclonal, and can be used for diagnostic, purification or therapeutic purposes. For example, the antibodies of the subject invention could be used to purify protein B, or fragments thereof, from a crude mixture of components.

The subject invention further concerns polynucleotide sequences which encode the novel IgA-binding polypeptides disclosed herein. These polynucleotide sequences can be readily constructed by those skilled in the art having the knowledge of the amino acid sequences of the subject polypeptides. As would be appreciated by one skilled in the art, a number of different polynucleotide sequences can be constructed due to the degeneracy of the genetic code. The choice of a particular nucleotide sequence could depend, for example, upon the codon usage of a particular expression system. In addition, fragments and variants of the polynucleotide can be readily prepared by the skilled artisan. For example, by using the Bal31 exonuclease (Wei et al., 1983), the skilled artisan can systematically remove nucleotides from either or both ends of the polynucleotide to generate a spectrum of polynucleotide fragments. Accordingly, the subject invention encompasses these fragments and variants of the polynucleotide molecule.

The IgA-binding polypeptides of the subject invention can be prepared by a number of different methods known to the ordinarily skilled artisan. The polypeptides can be synthesized using standard peptide synthesis techniques known in the art, including solid phase synthesis techniques such as BOC and FMOC (Merrifield, 1963). Alternatively, recombinant DNA technology may be employed for the expression of a desired polypeptide in a host cell transformed with an expression vector comprising a polynucleotide sequence that encodes the subject polypeptide. The polypeptides of the subject invention can be purified using gel filtration, ion exchange chromatography, affinity chromatography, HPLC or other purification techniques known in the art.

The scope of the subject invention is intended to cover not only the specific amino acid sequences of the IgA-binding polypeptides disclosed herein, but also includes amino acid sequences of polypeptides having IgA-binding activity comparable to the specifically exemplified polypeptides. For example, polypeptides that are somewhat longer or shorter than the polypeptides exemplified herein are included within the scope of the subject invention. Preferably, any added amino acids would be the same as the corresponding amino acids of the native protein B. Also within the scope of the subject invention are polypeptides which have substantially the same amino acid sequences of the polypeptides exemplified herein except for one or more amino acid alterations (substitutions, additions, or deletions), wherein the alteration does not substantially diminish IgA-binding activity.

The IgA-binding polypeptides of the subject invention can be combined with other proteins to produce novel hybrid proteins possessing useful and advantageous properties. Hybrid proteins can be produced by ligating polynucleotide sequences encoding an amino acid sequence of the subject polypeptides with polynucleotides encoding the desired regions of other proteins. For example, a hybrid protein can be prepared which has the ability to bind to both IgA and other immunoglobulins, such as IgG, by ligating a polynucleotide sequence encoding an amino acid sequence of the subject polypeptides with polynucleotides encoding an IgG binding domain of protein G or protein A. A hybrid protein having the ability to bind both IgA and IgG can be used to isolate or detect both IgA and IgG. The IgG binding domains of protein G and protein A are known to those skilled in the art. The polynucleotide sequence encoding the novel hybrid protein can then be transformed into appropriate host cells which can express the recombinant hybrid protein.

Hybrid polypeptides can also be produced using standard peptide synthesis methods. The amino acid sequence of an IgA-binding polypeptide of the subject invention can be synthesized in conjunction with the amino acid sequence of another polypeptide whose sequence is known in the art. Alternatively, peptides can be covalently joined in peptide linkage with other peptides, or with other peptide sequences, via intervening linker peptides. The linker peptide can contain one or more amino acid residues randomly selected from any of the commonly known amino acids.

Following are examples which illustrate procedures, including the best mode, for practicing the invention. These examples should not be construed as limiting. All percentages are by weight and all solvent mixture proportions are by volume unless otherwise noted.

EXAMPLE 1

Coupling of Protein B to an Active Support

A recombinant Protein B polypeptide as described in U.S. Pat. No. 5,413,918, was produced using standard methods. The recombinant Protein B was coupled to different support matrices, including HIPAC chromatographic media (ChromatoChem, Inc., Missoula, Mont.), described in U.S. Pat. No. 5,240,602, and CNBr-activated SEPHAROSE (Pharmacia Biotech, Uppsala, Sweden), according to the manufacturer's protocol. The optimal pH conditions for coupling of Protein B to the HIPAC support matrix were found to be in the range of about 6.0 or less. Samples of human serum containing IgA were passed over the immunoabsorbents and the amount of IgA removed from the serum determined. As can be seen in Table 1, both the Protein B-coupled HIPAC and SEPHAROSE support matrices were effective in depleting human IgA from a serum sample.

TABLE 1

| Type of Matrix | IgA depleted from 0.5 ml Human Serum | IgA eluted from Column |
| --- | --- | --- |
| CNBr-Sepharose | 58% | 25% |
| LTQ | 75% | 50% |

Figure 1B:
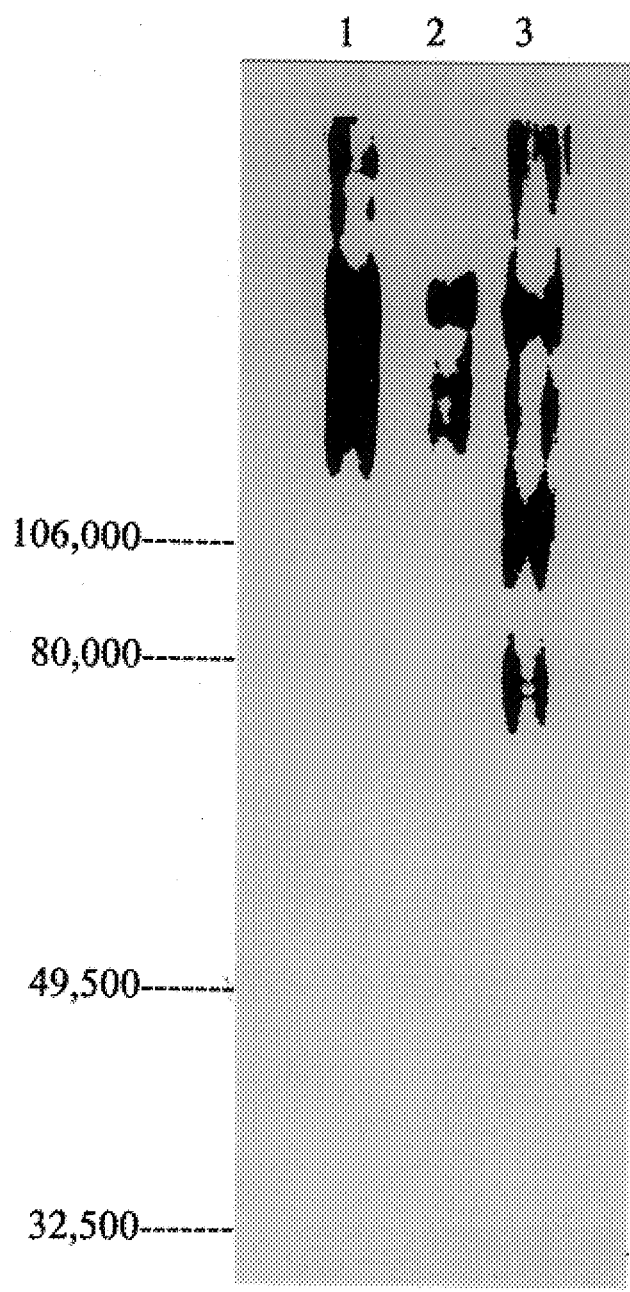

As seen in FIGS. 1A–1B, the Protein B-coupled HIPAC support removed only the IgA from the sample, leaving all other components remaining within the serum. The IgA-binding activity of the support matrix was found to remain stable after exposure to numerous reagents such as acetic acid, chaotrophic agents, high salt detergents, and different pH buffers. Because the initial step in the purification of the recombinant Protein B involves placing the bacteria that produce Protein B in boiling water, heat sterilization can be used for the immunoadsorbent support matrix without destroying IgA binding activity.

EXAMPLE 2

Coupling of Protein B to a Solid Support Through the Terminal Amines Using Citraconic Anhydride In an alternative method for coupling Protein B to a solid support, non-recombinant native Protein B was first modified by blocking all available terminal amines using the reversible reagent citraconic anhydride as described by Attasi et al., (1972), incorporated herein by reference. Briefly, Protein B was first dissolved in 0.1 M Na Borate, pH 8.6 at 2 mg/ml. Three aliquots of citraconic anhydride were added sequentially to the protein solution and the mixture incubated at room temperature for 30 minutes after each addition. The mixture was allowed to react for an additional 2 hours at room temperature after the final addition. The mixture was dialyzed against 0.1M carbonate, pH 10.0 overnight at 4° C. A small aliquot was removed and tested for free amine groups using the TNB assay as described in Anal. Biochem. (1975) 64:284–288, incorporated herein by reference. If any development of yellow color was observed, the mixture was returned for further reaction with the citraconic anhydride. Once the mixture tested negative for free amine groups, the dialyzed Protein B was added directly to an epoxy-activated solid support and incubated at room temperature for 24 hours. The Protein B solution was then separated from the support and the amount of unreacted Protein B measured in the solution. The support was then washed extensively with distilled water, followed by extensive washing in 0.1M citrate buffer (pH 4.0) and incubated overnight in the same buffer. After the overnight incubation, the support was again washed extensively with distilled water and resuspended in PBS.

The Protein B-coupled support matrix was then tested for IgA binding capacity. The Protein B-coupled support matrix removed 1 mg of IgA for each mg of Protein B used in the coupling reaction. This procedure produced an IgA immunoadsorbent approximately 10-fold more active than the coupling procedure used in Example 1.

EXAMPLE 3

Determination of the Protein B Active IgA Combining Site

An IgA-binding region of Protein B was elucidated as follows: two oligonucleotide primers were synthesized, oligo 1 (SEQ ID NO. 1) starting from the 5' end of the gene encoding the mature protein and oligo 2 (SEQ ID NO. 2) corresponding to that region just short of the 3' end of the gene:

oligo 1: 5'-AGTGAGCTTGTAAAGGACGAT-3' (SEQ ID NO. 1)

oligo 2: 5'-TACATCAACAACGGAAAAGAAA-3' (SEQ ID NO. 2)

Using chromosomal DNA from a Group B streptococcal strain containing the Protein B gene as a template and employing standard PCR procedures, an amplification product of approximately 3.2 kb was produced when PCR amplification products were electrophoresed on a 1% agarose gel. The PCR product containing Protein B polynucleotide sequence was cleaved with the endonuclease restriction enzymes BamHI and PstI. The BamHI site was created in the oligo 1 primer (SEQ ID NO. 1) used for the PCR amplification. The PstI site is contained within the Protein B gene sequence (Jerlström et al. 1991).

The DNA restriction fragments were electrophoresed on a 1% agarose gel, and the larger fragment was excised and purified using procedures described in *Current Protocols in Molecular Biology* (1993) Volume 1, Supplements 25 and 26, incorporated herein by reference. The BamHI-PstI DNA fragment was then ligated into an appropriately restricted T7 expression plasmid pET17b (Novagen, Inc., Madison, Wis.) using a standard T4 ligase procedure. The plasmid was then transformed into *E. coli* strain BL21(DE3) (Novagen, Inc.) using the manufacturer's suggested protocols. Transformed *E. coli* cells containing the plasmid were plated out and selected on LB plates containing 50 µg/ml carbenocillin. The surviving colonies were blotted onto nitrocellulose and tested for IgA-binding activity using the BCIP-NBT method (Blake et al., 1984). Several colonies demonstrating high IgA-binding capacity were selected and grown overnight in 1 ml LB broth containing carbenocillin at 30° C. These cultures were then diluted 1 to 100 into fresh LB-carbenocillin broth and incubated at 30° C. for an additional 6 hours. Expression was then induced by the addition of IPTG and the culture continued for an additional 2 hours at 30° C. The cells were collected by centrifugation, resuspended in water and subjected to several freeze-thaw cycles. The cells were once again collected by centrifugation and the supernates saved for examination of their IgA-binding activity.

A stable plasmid producing recombinant Protein B was isolated and the "NOVATOPE" Epitope Mapping System (Novagen, Inc.) was then utilized according to the manufacturer's instructions. The purified plasmid containing Protein B gene sequence was randomly digested with DNase I and electrophoresed in a 2% low melting point agarose gel. Fragments of the DNA corresponding to sizes between 50 to 150 base pairs were excised from the gel, purified, and resuspended in TE buffer. A single dA was added to the fragments using the recommended reaction mixture and the fragments were then ligated into the pTOPE T-vector. The pTOPE vector contains single dT ends. After a standard ligation procedure, the plasmids were transformed into competent NOVABLUE (DE3) cells (Novagen, Inc.) and plated on LB plates containing 50 µg/ml carbenicillin and 12 µg/ml tetracycline. These plates were incubated overnight at 37° C.

The transformant colonies were carefully lifted onto nitrocellulose filters and the bacteria lysed by placing the filters into a chloroform vapor chamber for 15 minutes at room temperature. After the filters were removed from the chamber, they were placed, colony-side up, onto a Whatman 3MM filter which had been previously saturated with 20 mM Tris-HCl, pH 7.9, 6M Urea, and 0.5M NaCl. After 15 minutes, the filters were washed three times in PBS and incubated for 1 hour with purified human IgA in PBS-Tween. The filters were then rewashed in PBS-Tween and bound IgA detected using a goat anti-mouse Ig-alkaline phosphatase conjugate (Cappel Research Products, West Chester, Pa.) according to standard procedures (Blake et al., 1984). Twelve clones were selected on the basis of their binding to human IgA. The bacteria from each of these clones were inoculated separately onto fresh LB plates and retested for their IgA-binding ability as before. Plasmid preparations were made from each clone by standard means and the cloned gene fragments sequenced.

The nucleotide sequences of the cloned Protein B gene fragments were determined using the dideoxy method with denatured double-stranded plasmid DNA as the template as described in *Current Protocols in Molecular Biology* (1993). SEQUENASE II kits (United States Biochemical Corp., Cleveland, Ohio) were used in accordance with the manufacturers instructions. Three synthesized oligonucleotide primers (Operon Technologies, Inc., Alameda, Calif.) were used for the sequencing reactions: oligo 3 (SEQ ID NO. 3) for the 5' end, and oligo 4 (SEQ ID NO. 4) and oligo 5 (SEQ ID NO 5) for the 3' end:

oligo 3 5'-TCAAGCTTGGTACCGAGCTC-3' (SEQ ID NO. 3)

oligo 4 5'-TITGTTAGCAGCCGGATCTG-3' (SEQ ID NO. 4)

oligo 5 5'-CTCAAGACCCGTTTAGAGGCC-3' (SEQ ID NO. 5)

The sequence of all clones varied somewhat but all contained the nucleotide sequence:
5'-AATATTGACAAAGAGCTTAATCATCAAAAAAGTC AAGTTGAAAAAATGGCAGAGCAAAAGGGAAT CAC AAATGAAGATAAAGATCT-3' (SEQ ID NO. 6)

The polynucleotide molecule having the sequence shown in SEQ ID NO. 6 codes for the amino acid sequence:
Asn-Ile-Asp-Lys-Glu-Leu-Asn-His-Gln-Lys-Ser-Gln-Val-Glu-Lys-Met-Ala-Glu-Gln-Lys-Gly-Ile-Thr-Asn-Glu-Asp-Lys-Asp-Ser (SEQ ID NO. 7)

EXAMPLE 4

Synthesis of a Protein B IgA Combining Site on a Solid Support

Peptides having the amino acid sequence shown in SEQ ID NO. 7 were synthesized using NMP t-butoxycarbonyl chemistry on an ABI 430A peptide synthesizer (Applied Biosystems, Foster City, Calif.) and were deprotected. Peptides from a sample of the resin were removed from the resin by treatment with HF in the presence of anisole (0° C./1 h). Preparative purification of these peptides was performed using a C18 column (2.14 ID×30 cm) (Dynamax-Rainin, Woburn, Mass.). The peptides were quantitated by PTC amino acid analysis using a Waters PICOTAG system (Waters, Milford, Mass.). The synthesized peptides eluted from the C18 column as a major peak comprising about 75–85% of the total elution profile. The amino acid composition of the purified peptides were in agreement with the amino acid sequence which was used to synthesize the peptides.

Peptide synthesized on the solid support resin was then tested for the ability to bind to and remove IgA from human serum. The results showed that the synthesized polypeptide bound approximately 20 mg of human IgA per ml of resin.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Patents
U.S. Pat. No. 4,223,672.
U.S. Pat. No. 4,801,449.
U.S. Pat. No. 5,122,112.
U.S. Pat. No. 4,757,134.
U.S. Pat. No. 5,413,918.
Foreign Applications and Patents
European Application No. A1 0290707.
European Application No. A1 0367890.
Other References
Anonymous (1975) *Anal. Biochem.* 64:284–288.
Anonymous. (1993) *Current protocols in molecular biology.* John Wiley & Sons, New York, N.Y.
Anonymous. (1994) *AIDS* 8:911–921.
Apicella, M. A., M. A. J. Westerink, S. A. Morse, H. Schneider, P. A. Rice, J. M. Griffiss (1986) *J. Infect. Dis.* 153:520–526.
Attasi, M. Z. and A. F. S. A. Habeeb, (1992) *Methods in Enzymology*, Vol. XXV, Enzyme Structure, Part B, Academic Press, New York.
Birx, D. L., J. L. Rhoads, J. C. Wright, D. S. Burke, R. R. Redfield (1991) *J. Acq. Imm. Def. Syn.* 4:188–196.
Blake, M. S., K. H. Johnston, G. J. Russell-Jones, E. C. Gotschlich (1984) *Analyt. Biochem.* 136:175–179.
Conlon, C. P. (1993) *Brit. Med. Bull.* 49:412–422.
Dabrow, M. B., J. C. Wilkins (1993) *Postgrad. Med.* 93:183–190.
Eckrich, R. J., D. M. Mallory, S. G. Sandler (1993) *Transfusion* 33:488–492.
Faulmann, E. L., J. L. Duvall, M. D. P. Boyle (1991) *Biotechniques* 10:748–755.
Filipovich, A. H., A. Mathur, D. Kamat, J. H. Kersey, R. S. Shapiro (1994) *Immunodeficiency* 5:91–112.
Griffiss, J. M. (1975) *J. Immunol.* 114:1779–1784.
Griffiss, J. M. (1982) *Infection* 10:246–251.
Griffiss, J. M. (1983) *Ann. N. Y. Acad. Sci.* 409:697–707.
Griffiss, J. M., M. A. Bertram (1977) *J. Infect. Dis.* 136:733–739.
Griffiss, J. M., D. K. Goroff (1983) *J. Immunol.* 130:2882–2885.
Guerra, E., C. von Hunolstein, I. Quinti, S. Recchia, M. Stegagno, E. Visconti, G. Orefici (1992) *Int. J. Med. Microbiol. Virol ParasitoL Infect. Dis.* 276:429–436.
Gupta, S. C., J. Agarwal, P. A. Singh, N. K. Mehdiratta, N. K. Keswani (1994) *Ind. J. Pathol. Microbiol.* 37:319–326.
Jerlström, P. G., G. S. Chhatwal, K. N. Timmis (1991) *Molec. Microbiol.* 5:843–849.
Lim, E. C., D. Chia, D. W. Gjertson, P. Koka, P. I. Terasaki (1993) *Transplantation* 55:996–999.
Misbah, S. A, H. M. Chapel (1993) *Drug Safety* 9:254–262.
Merrifield, R. B. (1963) *J. Amer. Chem. Soc.* 85:2149.
Musher, D. M., A. Goree, R. E. Baughn, H. H. Birdsall (1984) *Infect. Immun.* 45:36–40.
Quesnel, A., P. Moja, S. Blanche, C. Griscelli, C. Genin (1994a) *Clin. exp. Immunol.* 97:380–385.
Quesnel, A., P. Moja, F. Lucht, J. L. Touraine, B. Pozzetto, C. Genin (1994b) *Gut* 35:803–808.
Rhoads, J. L., D. L. Birx, D. C. Wright, J. F. Brundage, B. L. Brandt, R. R. Redfield, D. S. Burke (1991) *J. Acq. Imm. Def. Syn.* 4:724–731.
Russell-Jones, G. J., P. L. Ey, B. L. Reynolds (1980) *Molec. Immun.* 17:1173–1180.
Russell-Jones, G. J., P. L. Ey, B. L. Reynolds (1981) *Intl. Arch. Allergy* 66:316–325.
Russell-Jones, G. J., E. C. Gotschlich, M. S. Blake (1984) *J. Exp. Med.* 160:1467–1475.
Sandler, S. G., D. Mallory, D. Malamut, R. Eckrich (1995) *Trans. Med. Rev.* 9:1–8.
Taylor, P. W. (1972) *Clinical Science* 43:23–30.

I claim:

1. An immunoadsorbent composition comprising an IgA-binding composition coupled to a solid support matrix, wherein said IgA-binding composition comprises an IgA-binding fragment of Protein B consisting of an amino acid sequence of SEQ ID NO. 7.

2. The composition, according to claim 1, wherein said IgA-binding fragment of Protein B is coupled to said solid support matrix by blocking terminal amines of said IgA-binding fragment of Protein B using citraconic anhydride and coupling said IgA-binding fragment of Protein B to an epoxy-activated support.

3. The composition, according to claim 1, wherein said IgA-binding fragment of said Protein B is chemically synthesized directly on said solid support matrix.

4. The composition, according to claim 1, wherein said solid support matrix is selected from the group consisting of glass, nylon, particulate silica, polystyrene, polyethylene, polyamides, polyacrylamides, polyvinyls, polypropylene, cellulose, agarose, dextran, CNBr-activated SEPHAROSE, and HIPAC chromatographic media.

5. A method for treating an immunocompromised patient having elevated levels of IgA, said method comprising:

(a) contacting an IgA-containing biological fluid obtained from the patient with an IgA-binding immunoadsorbent composition of claim 1 under conditions suitable for binding between said immunoadsorbent composition and said IgA; and (b) reinfusing said contacted biological fluid into the patient.

6. The method, according to claim 5, wherein the patient is immunocompromised due to a condition selected from the group consisting of infection with HIV, treatment with chemotherapy, and treatment with an immunosuppressive drug.

7. The method, according to claim 5, wherein said IgA-containing biological fluid is selected from the group consisting of blood, plasma, and serum.

8. The method, according to claim 5, wherein said IgA-containing biological fluid is removed from the patient in a continous manner and steps (a) and (b) are performed while additional IgA-containing biological fluid is being removed from the patient.

9. The method, according to claim 5, wherein steps (a) and (b) are performed on a discrete volume of IgA-containing biological fluid.

10. The method, according to claim 5, wherein said IgA-containing biological fluid is separated into cellular components and fluid components prior to performing step (a) and said cellular components are reinfused back into the patient.

11. The method, according to claim 5, wherein said solid support matrix is selected from the group consisting of glass, nylon, particulate silica, polystyrene, polyethylene, polyamides, polyacrylamides, polyvinyls, polypropylene, cellulose, agarose, dextran, CNBr-activated SEPHAROSE, and HIPAC chromatographic media.

12. An IgA binding composition comprising an IgA binding fragment of Protein B consisting of an amino acid sequence of SEQ ID NO. 7.

\* \* \* \* \*

UNITED STATES PATENT AND TRADEMARK OFFICE
CERTIFICATE OF CORRECTION

PATENT NO.    : 5,869,047
DATED         : February 9, 1999
INVENTOR(S)   : Milan Blake It is certified that error appears in the above-identified patent and that said Letters Patent is hereby corrected as shown below:

Item [54] Title:

"Method For Therapeutically Treating Immunocomprised Persons" should read
-- Methods For Therapeutically Treating Immunocompromised Persons --.

Signed and Sealed this

Fourteenth Day of August, 2001

Attest:

*Attesting Officer*

NICHOLAS P. GODICI
*Acting Director of the United States Patent and Trademark Office*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:1:

AGTGAGCTTG TAAAGGACGA T          21

( 2 ) INFORMATION FOR SEQ ID NO:2:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:2:

TACATCAACA ACGGAAAAGA AA          22

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:3:

TCAAGCTTGG TACCGAGCTC          20

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:4:

TTTGTTAGCA GCCGGATCTG          20

( 2 ) INFORMATION FOR SEQ ID NO:5:

( i ) SEQUENCE CHARACTERISTICS:
        ( A ) LENGTH: 21 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:5:

-continued

```
CTCAAGACCC  GTTAGAGGC  C                                                                      21
```

( 2 ) INFORMATION FOR SEQ ID NO:6:

( i ) SEQUENCE CHARACTERISTICS:
        ( A ) LENGTH: 87 bases
        ( B ) TYPE: nucleic acid
        ( C ) STRANDEDNESS: single
        ( D ) TOPOLOGY: linear ( i i ) MOLECULE TYPE: DNA ( i x ) SEQUENCE DESCRIPTION: SEQ ID NO:6:

```
AATATTGACA  AAGAGCTTAA  TCATCAAAAA  AGTCAAGTTG  AAAAAATGGC  AGAGCAAAAG      60

GGAATCACAA  ATGAAGATAA  AGATTCT                                            87
```

( 2 ) INFORMATION FOR SEQ ID NO:7:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( i x ) SEQUENCE DESCRIPTION: SEQ ID NO:7:

```
Asn  Ile  Asp  Lys  Glu  Leu  Asn  His  Gln  Lys  Ser  Gln  Val  Glu  Lys  Met
1                   5                        10                       15

Ala  Glu  Gln  Lys  Gly  Ile  Thr  Asn  Glu  Asp  Lys  Asp  Ser
                    20                       25
```